(12) United States Patent
Ad

(10) Patent No.: US 7,416,551 B2
(45) Date of Patent: Aug. 26, 2008

(54) CATHETER FOR DELIVERING A TISSUE ABLATION PROBE

(75) Inventor: Niv Ad, Tel Aviv (IL)

(73) Assignee: A.F.M. Medical Systems Ltd., Tel Aviv (IL)

( * ) Notice: Subject to any disclaimer, the term of this patent is extended or adjusted under 35 U.S.C. 154(b) by 226 days.

(21) Appl. No.: 10/900,396

(22) Filed: Jul. 28, 2004

(65) Prior Publication Data

US 2005/0113743 A1 May 26, 2005

Related U.S. Application Data

(60) Provisional application No. 60/490,263, filed on Jul. 28, 2003.

(51) Int. Cl.
*A61B 18/18* (2006.01)

(52) U.S. Cl. .......................... 606/41; 607/101

(58) Field of Classification Search .................. 606/41, 606/45–50; 607/101–102
See application file for complete search history.

(56) References Cited

U.S. PATENT DOCUMENTS

| 5,830,209 | A | * | 11/1998 | Savage et al. | 606/15 |
| 5,906,613 | A | | 5/1999 | Mulier et al. | |
| 5,931,848 | A | | 8/1999 | Saadat | |
| 6,071,279 | A | * | 6/2000 | Whayne et al. | 606/41 |
| 6,280,441 | B1 | * | 8/2001 | Ryan | 606/45 |
| 6,491,689 | B1 | | 12/2002 | Ellis et al. | |
| 6,702,811 | B2 | * | 3/2004 | Stewart et al. | 606/41 |
| 2003/0078575 | A1 | | 4/2003 | Jahns et al. | |

FOREIGN PATENT DOCUMENTS

DE 195 37 084 A1 4/1997
EP 0 797 958 A1 10/1997

* cited by examiner

*Primary Examiner*—Michael Peffley
(74) *Attorney, Agent, or Firm*—The Nath Law Group; Jerald L. Meyer; Matthew J. Moffa

(57) ABSTRACT

A delivery catheter having a shaft with a distal end and a proximal end for delivering an ablation probe to a body site. The delivery catheter comprises mounting members located at the distal end configured to receive an ablation probe; and attachment members configured to attach the distal end to a tissue surface. The delivery catheter preferably configured to allow an ablation probe mounted on the distal end to be manipulated so as to extend from the distal end in a direction selected from a range of directions. Even more preferably, the delivery catheter is configured to allow an ablation probe mounted on the distal end to be manipulated so as to move along a tissue surface and perform linear ablation. The invention also provides a system comprising the delivery catheter of the invention and an ablation device having an ablation probe, wherein the delivery catheter and the ablation probe are configured to allow the ablation probe to be mounted at the distal end of the delivery catheter.

19 Claims, 20 Drawing Sheets

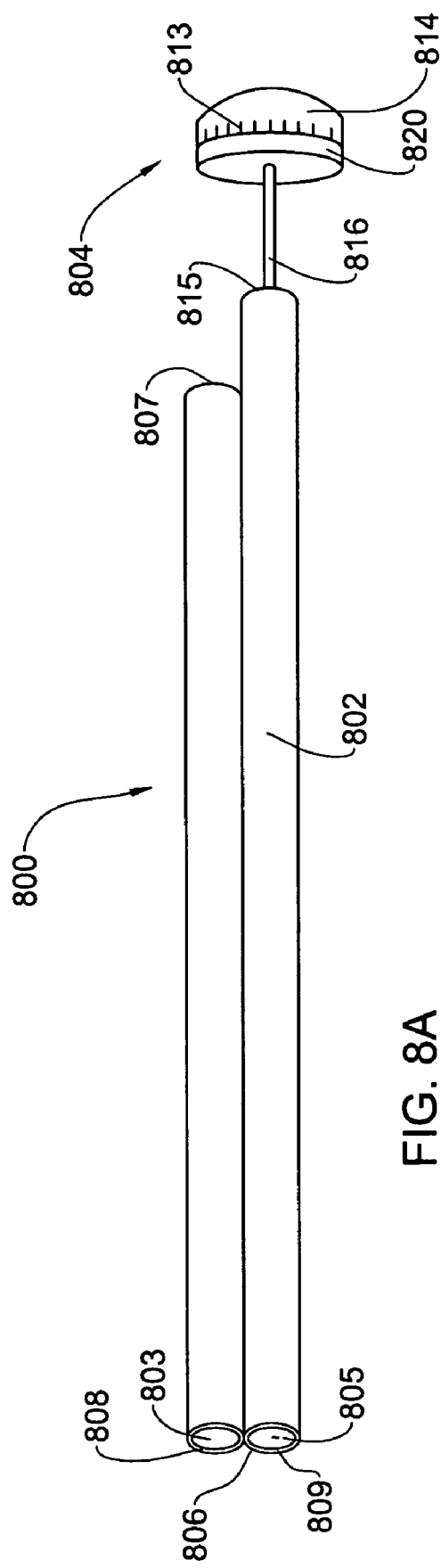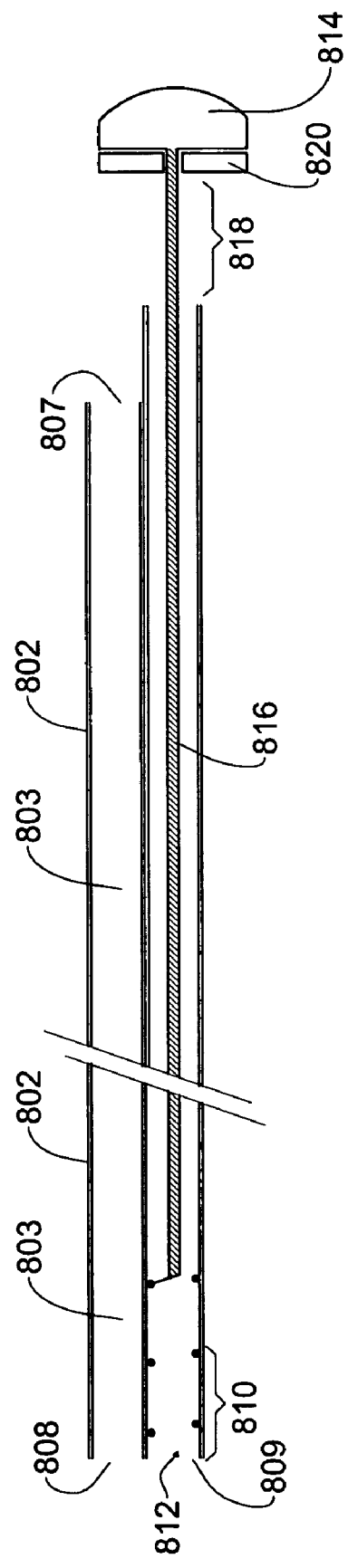
FIG. 8A
FIG. 8B

CATHETER FOR DELIVERING A TISSUE ABLATION PROBE

This application claims the benefit of prior U.S. provisional patent application No. 60/490,263 filed Jul. 28, 2003, the contents of which are hereby incorporated by reference in their entirety.

FIELD OF THE INVENTION

The present invention is generally in the field of medical devices. More specifically, the invention concerns delivery catheters for delivering an object to a body site.

BACKGROUND OF THE INVENTION

Medical refractory cardiac arrhythmia can be treated using catheter ablation techniques. However, ablation of cardiac tissue along a continuous trace over a tissue surface (referred to herein as "linear ablation") is difficult to achieve by this technique. Linear ablation in cardiac tissue is an accepted procedure for treating arrhythmias, such as atrial fibrillation, which is the most common cardiac arrhythmia. In this procedure, more than one line of tissue ablation is usually needed for successful treatment. However, generating continuous ablation lines in catheter ablation techniques is difficult to achieve. Thus, rather than utilizing the generally preferred per-cutaneous catheter ablation technique that makes use of an ablation catheter, ablation is carried out in an open-heart procedure in which the chest of the treated individual is opened to expose the heart tissue. While the open heart procedure is more traumatic and fully invasive, it is none the less become the standard ablation procedure. At times, ablation needs to be performed on heart portions that face the pulmonary veins. The lack of a direct view of these regions by the surgeon during an open heart procedure complicates the open heart ablation procedure.

SUMMARY OF THE INVENTION

In its first aspect, the present invention provides a delivery catheter for delivering an ablation probe to a site within the body in order to perform ablation of tissue at the site. The delivery catheter is configured to carry an ablation probe near the distal end of the catheter. The delivery catheter comprises means for attaching the distal end of the delivery catheter to a tissue surface at the site. The delivery catheter is also configured to allow the ablation probe to extend from the delivery catheter and to be manipulated in a body cavity so as to contact a tissue surface at a selectable location on the site and to ablate the tissue at that location. Manipulating the ablation probe also allows linear ablation along a selectable trace over the tissue surface at the site to be performed.

The distal end of the delivery catheter carrying the ablation probe is delivered to the body site where ablation is to be carried out. The distal end of the catheter is then affixed to a tissue surface at the site. The ablation probe is then manipulated so as to extend out from the catheter and contact the tissue surface at a desired location at the site in order to carry out tissue ablation at that location. The probe may be manipulated so as to carry out linear ablation over a tissue surface at the site.

The invention also provides a system comprising a delivery catheter of the invention and a tissue ablation device having an ablation probe. The delivery catheter and the ablation device are configured to allow the ablation probe to be carried by the delivery catheter at the distal end for the delivery catheter. The ablation device also preferably includes a utility for delivering ablative energy that may be heat or cold, to the probe. The ablation probe delivers the ablating energy to the tissue in contact therewith. The ablating energy delivered by the ablation probe can be in the form of Radio-Frequency (RF), microwave, laser, ultrasound, heat, cryo energy, etc. As will be appreciated, the invention is not limited to any specific ablation catheter. The probe may be essentially straight although it may also be curved or even define a closed loop.

The system may also include a guide wire that is first delivered to a body site where ablation is to be performed. The delivery catheter carrying the ablation probe on its distal end is then mounted on the guide wire and delivered to the site along the guide wire. For example, the delivery catheter may be delivered into the left atrium through the intra-atrial septum.

The utility for delivering ablative energy to the probe is either linked to the probe or is associated therewith in an induction association to permit the delivery of ablative energy to the probe.

By a further aspect of the invention, there is provided a medical procedure that comprises: (a) mounting an ablation probe onto the distal end of a delivery catheter according to the invention; (b) delivering the distal end of the delivery catheter to a body site where tissue ablation is to be performed; (c) extending the ablation probe from the distal end of the delivery catheter and manipulating the ablation probe so as to contact at a desired location on a tissue surface at the site where ablation is to be performed; and (d) applying ablative energy to the tissue at the desired location at an intensity and for time to yield effective tissue ablation.

A person versed in the art should be able to determine both the intensity of the ablative energy and the length of time for its application. This may be determined, for example, on the basis of either the scientific literature relating to tissue ablation techniques, on his own experience, or by resorting to some limited set of experiments that may be carried out in a variety of animal models (e.g., in pigs) as well as on humans, within the framework of appropriate clinical trials, for determining both the intensity and the time needed to yield an effective tissue ablation.

The ablation energy that is delivered may be any form of energy, for example in the form of Radio-Frequency (RF), microwave, laser, ultrasound heat, cryo, etc. The probe is preferably made of a heat conducting material such as metal. The energy may, in accordance with one embodiment may be delivered from a source directly to the probe, as known per se. For example, the probe may have a lumen that is fed with an energy-delivering fluid, e.g. a cooled gas, from a source of such fluid, fed to the probe through the length of the delivery catheter via an appropriate ducting arrangement. The probe may also be provided with an internal electric heating device connected by wire leads running along the length of the delivery catheter to a power source. Additionally, heating of the probe may be achieved through an induction heating process. As is clear to the artisan, the invention is not limited to the type of ablative energy nor to any manner in which it is delivered to the probe. On the contrary, any energy-delivering technique used or otherwise known in the art may be employed in the system and catheter of the invention. As may also be appreciated, the above described ablation energy delivering means is not a conclusive list but is rather an example thereof.

According to one embodiment of the invention, the attachment arrangement includes an attachment body that defines a trough with an open side that faces the tissue to be ablated and accommodating said probe. Said probe may be firmly associated with the attachment body or alternatively, the attachment body may be designed so as to permit the probe to be manipulated from outside the body to move linearly within said trough. As an example of the latter probe design, the attachment body may be fitted at the distal end of the catheter and the probe guided in this way along the catheter into the trough of the attachment body.

The attachment body may comprise attachment members disposed on both sides of said probe for holding said body and the probe against said tissue. By one example, said attachment members are small hooks or micropods.

By another embodiment, said attachment members are a plurality of suction ducts or cups that attach to a tissue surface by negative pressure or vacuum. The attachment in this case is through the vacuum that forms within the cups. The cups may be passive vacuum cups with the vacuum being formed during the attachment process. Alternatively, and preferably, the vacuum may be an active one with each vacuum cup being linked via a conduit running through the delivery catheter to a vacuum source located outside the body.

A preferred but not exclusive implementation of the invention is in ablation of cardiac tissue. In this procedure a guide wire is inserted through an incision in the skin into a vein, typically a femoral vein and is guided first to the right atrium and from there to the left atrium through the inter-atrial septum. The delivery catheter of the invention carrying an ablation probe on its distal end is then mounted on the guide wire and delivered to the left or right atrium. Then the distal end fo the delivery catheter is attached to an internal surface of the atrium, and the tissue is ablated. The ablation design is typically based on the surgical Maze procedure and includes, encircling of the pulmonary veins and various ablation lines and points throughout both the right and the left atria. The same system can serve for ablation in the ventricles for ventricular arrhythmias. Other types of cardiac arrhythmias that can be treated by ablation include, but are not limited to, Ventricular Tachycardia (VT), Supra Ventricular Tachycardia (SVT), Atrial Flutter and Wolf Parkinson White (WPW). For the right ventricle the distal end of the delivery catheter may be inserted into the femoral vein and delivered to the right atrium then through the tricuspid valve to the right ventricle. For ablation in the left ventricle the distal end of the delivery catheter may be delivered to the left atrium as described above and then through the mitral valve to the left ventricle. In some cases the distal end of the catheter can be delivered to the left ventricle via the Aortic valve. Ablation can also be performed in the right atrium for certain arrhythmias originating in the right atrium.

Thus, in its first aspect, the invention provides a delivery catheter having a shaft with a distal end and a proximal end for delivering an ablation probe to a body site, comprising:

(a) mounting members located at the distal end configured to receive an ablation probe; and
(b) attachment members configured to attach the distal end to a tissue surface.

In its second aspect the invention provides a medical system comprising:

a delivery catheter of the invention; and
a tissue ablation device having an ablation probe;
wherein the delivery catheter and the ablation probe are configured to allow the ablation probe to be mounted at the distal end of the delivery catheter.

In its third aspect, the invention provides a method for ablating a body tissue, comprising:

(a) mounting an ablation probe onto the distal end of a delivery catheter of the invention;
(b) delivering the distal end of the delivery catheter to a body site where tissue ablation is to be performed;
(c) extending the ablation probe from the distal end of the delivery catheter and manipulating the ablation probe so as to contact one or more desired locations on a tissue surface at the site where ablation is to be performed; and
(d) applying ablative energy to the tissue at each of the one or more desired locations at an intensity and for time to yield effective tissue ablation.

BRIEF DESCRIPTION OF THE DRAWINGS

For a better understanding the invention will now be described with reference to some non-limiting specific embodiments shown in the annexed drawings. In the drawings.

DETAILED DESCRIPTION OF THE INVENTION

Figure 7A:
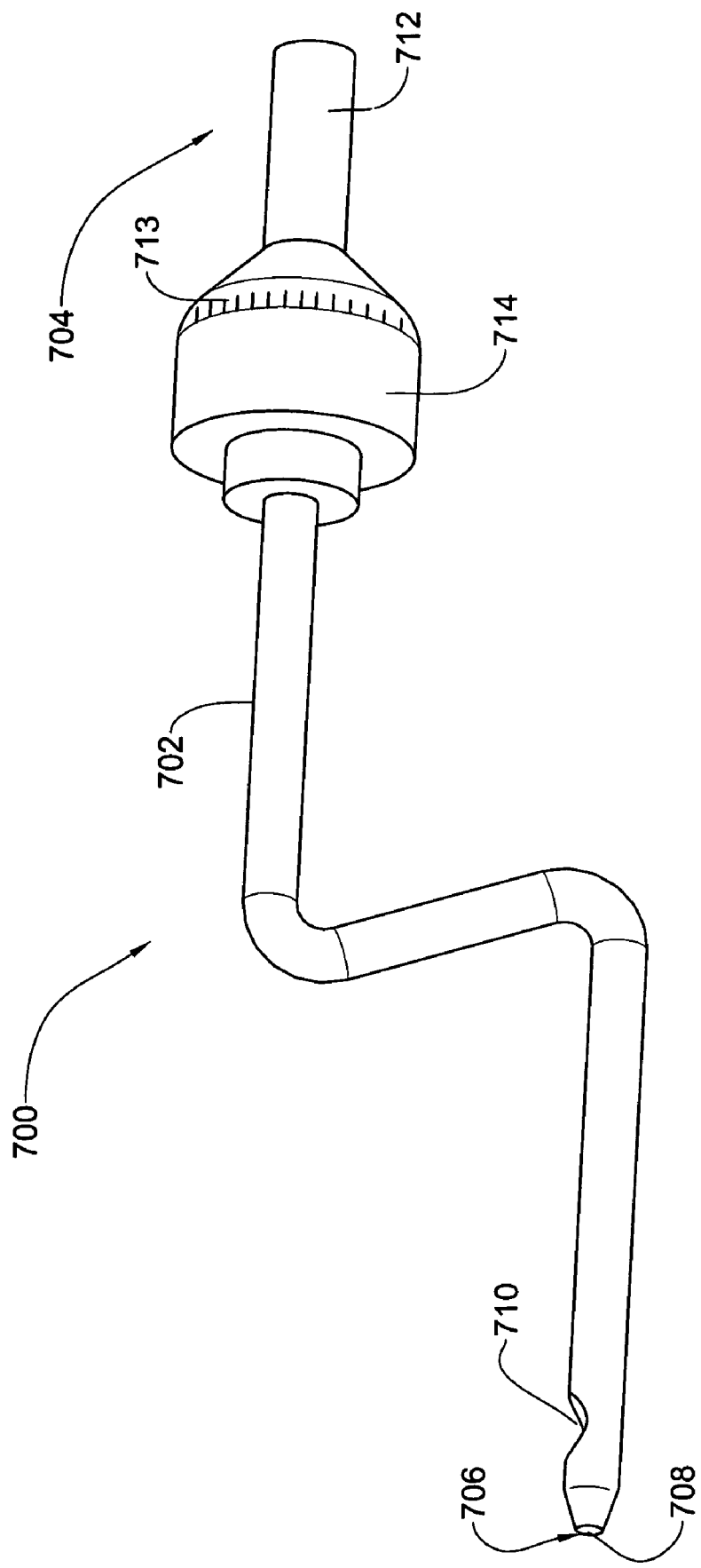
FIG. 7 shows a delivery catheter for an ablation device in accordance with one embodiment of the invention.

Referring first to FIG. 7, FIGS. 7a through 7f show a delivery catheter for delivering a tissue ablation probe to a body site, in accordance with one embodiment of the invention. As seen in FIG. 7a, the delivery catheter 700 has a slender flexible shaft 702 having a proximal end 704 and a distal end 706. The distal end 706 is tapered and terminates in a terminal opening 708. A side opening 710 is located in the wall of the shaft 702 near its distal end 706. The proximal end 704 of the catheter 702 has a handle 712 and a controller 714 described in detail below.

Figure 7B:
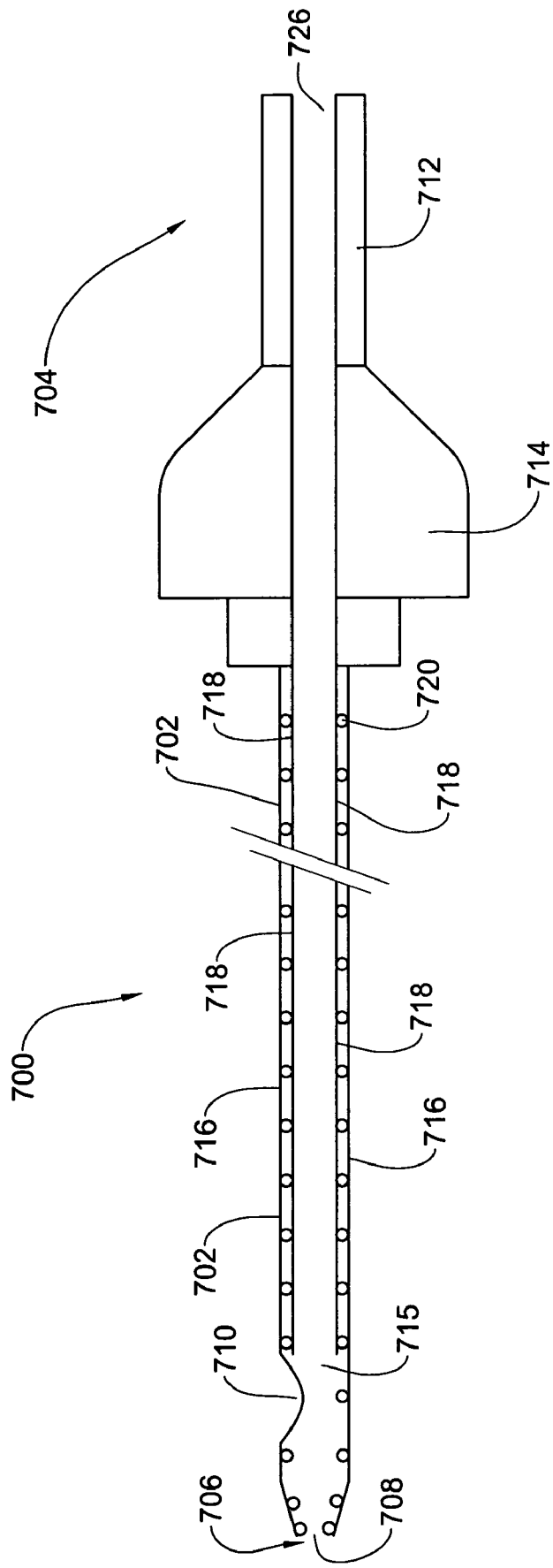

FIG. 7b shows the delivery catheter 700 in longitudinal section. The shaft 702 of the catheter 700 comprises an outer sheath 716. Within the outer sheath 716 is an inner sleeve 718. The inner sleeve 718 extends from an opening 726 in the handle 712 through the handle 712 and controller 714 through the outer sheath 716, and terminates in a distal end 715 just proximally to the side opening 710. A helical spring 720 located in the space between the outer sheath 716 and the inner sleeve 718 surrounds the inner sleeve 718.

Figure 7C:
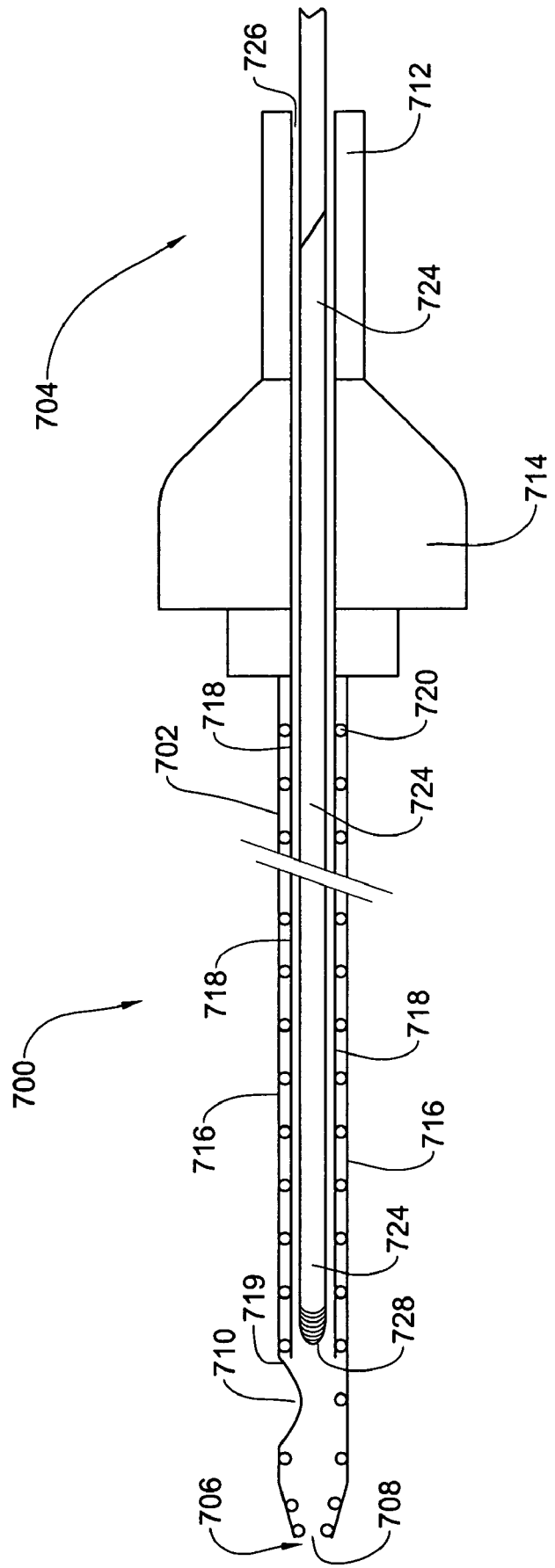

The inner sleeve 718 is configured to receive in its lumen the shaft of an ablation catheter. The inner sleeve 718 thus serves as a mounting member to allow the ablation catheter to be mounted onto the delivery catheter 700. FIG. 7c shows the delivery catheter 700 after an ablation catheter 724 has been inserted into the inner sleeve 718. The ablation catheter is inserted through the opening 726 at the end of the handle 712 and slides through the inner sleeve 718 until the distal end of the ablation catheter 724 is located at the distal end of the inner sleeve 718, which, as explained above, is adjacent and proximal to the opening 710. The ablation catheter 724 may be any type of ablation catheter known in the art and may use any type of ablative energy, such as radio frequency (RF) energy or cryo energy. The ablation catheter is connected at a proximal end (not shown) to a source of ablative energy (also not shown). The distal end of the ablative catheter includes a probe 728 for delivering ablative energy to a body tissue, as explained below.

With the delivery catheter 700 and the ablative catheter 724 in the configuration shown in FIG. 7c, the distal end 706 of the delivery catheter is inserted into the body and delivered to a body site where ablation of tissue is to be carried out. For example, a guide wire (not shown) may be inserted into the body through an incision in the skin and then delivered via the vasculature to a body site such as a heart, where ablation is to be carried out. The delivery catheter 700 may then be mounted on the guide wire and the distal end 706 delivered to the site where the ablation is to be carried out on the guide wire. Alternatively, the distal end 706 of the delivery catheter 700 may be delivered to an epicardial site in a beating heart surgical procedure.

Figure 7D:
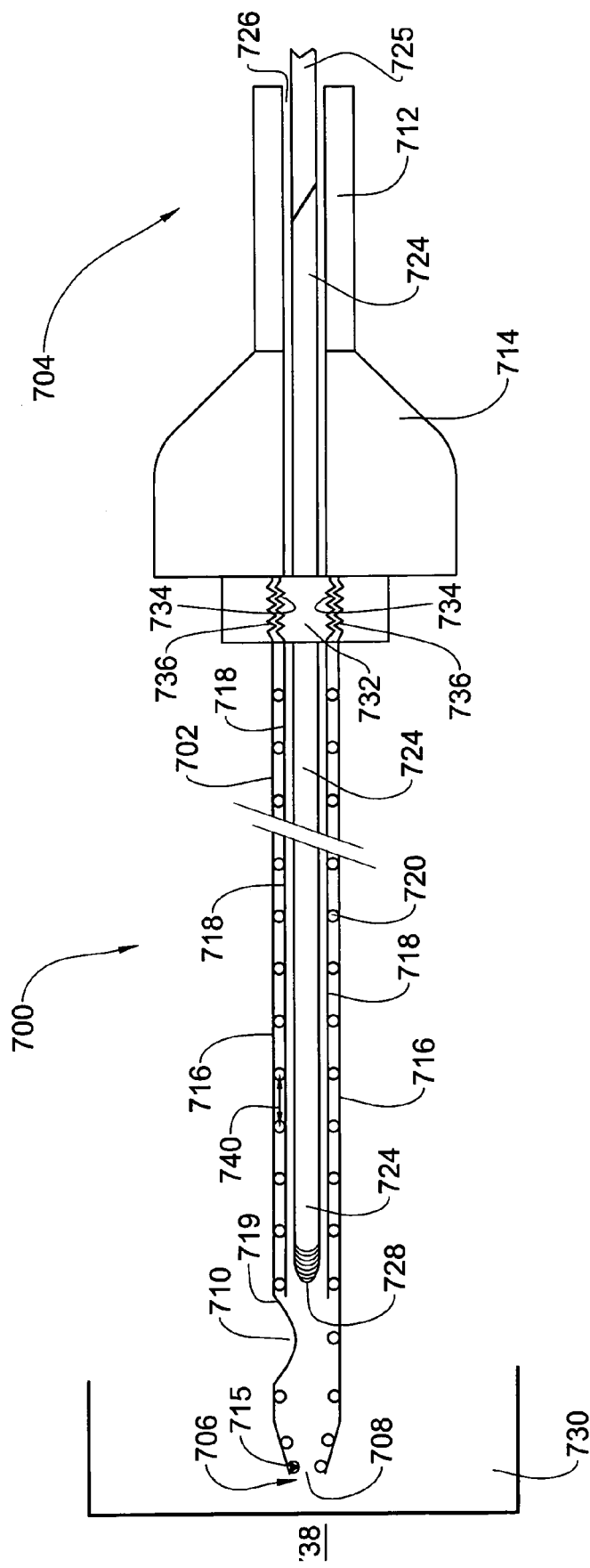

FIG. 7d shows the delivery catheter 700 after having been delivered to a body site where ablation is to be carried out. The site may be, for example, a body cavity 730 such as a heart ventricle. With the delivery catheter 700 in the arrangement shown in FIG. 7d, the control 714 is rotated. The control has a cylindrical extension 732 having a helical screw thread 734 on it outer surface that mates with a helical screw thread 736 on the inner surface of the outer sheath 716. Rotation of the control 714 in a clockwise direction when viewed from the proximal end 704 causes the extension 732 to progress towards the distal end 706 of the shaft 702. Graduation marks 713 on the controller 714 indicate the amount the controller 714 has been rotated from its original position. As the extension 732 progresses distally inside the shaft 702 it presses upon the spring 720. Pressing upon the spring 720 in this way causes the spring 720 to rotate inside the shaft 702 and to move distally through the shaft 702, so that the distal end of the spring 720 passes through the opening 708 and extends beyond the distal end 706 of the shaft 720.

Figure 7E:
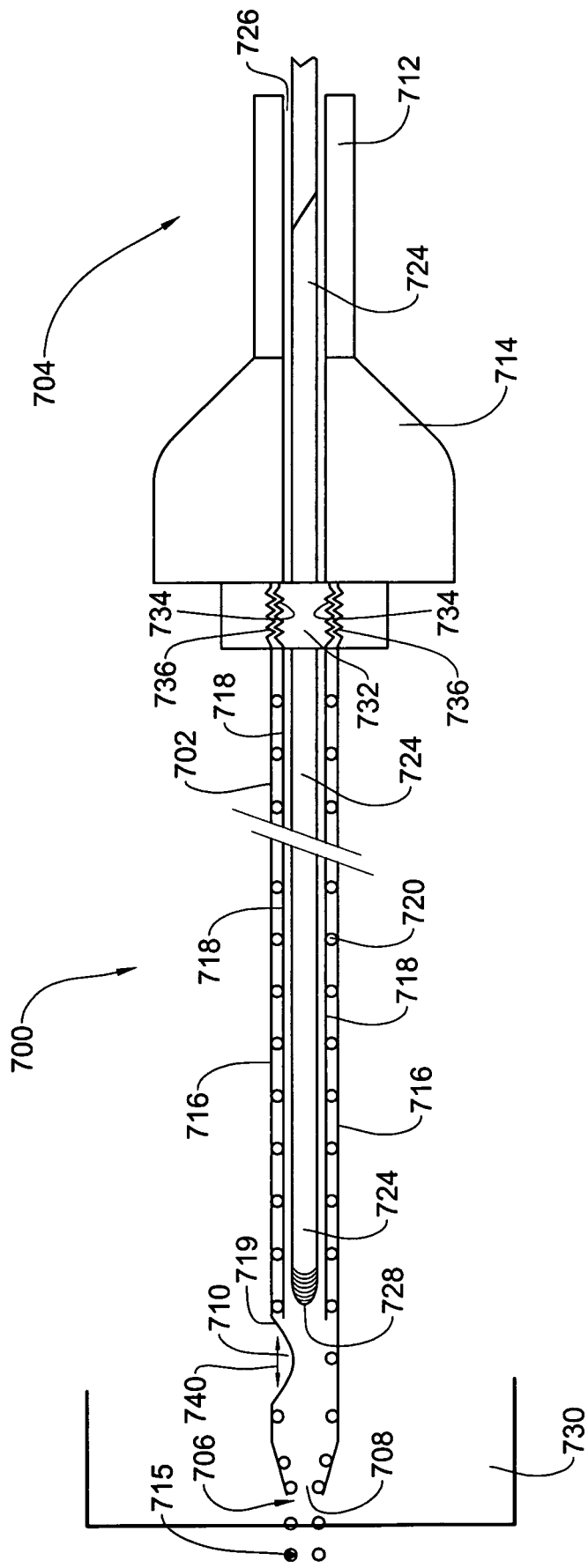

The spring 720 terminates at its distal end in a sharp point 715. Thus, as the spring 720 continues to be rotated, the portion of the spring 720 extending beyond the opening 708 screws into the body tissue 738 in the wall of the cavity 730, as shown in FIG. 7e so as to attach the distal end 706 of the delivery catheter 700 to the wall of the cavity 730. The controller 714 is provided with a locking mechanism (not shown) that prevents unwanted rotation of the controller.

At this point, the distal end of the ablation catheter 724 is made to pass through the side opening 710. This is carried out by grasping the exposed part 725 of the ablation catheter 724 extending from the opening 726 in the handle 712 and sliding the ablation catheter 724 distally. The spacing between adjacent turns of the helical spring 720 is less than the diameter of the ablation catheter, so that the ablation catheter is prevented from passing between adjacent turns of the spring 720. However, one turn of the spring 720, indicated by the arrow 740 in FIGS. 7d and 7e is wider than the other turns of the helical spring 720. The spacing of the turn 740 is greater that the diameter of the ablation catheter 724 and in the configuration of the delivery catheter 700 shown in FIG. 7e, with the helical spring 720 screwed into the tissue 738, the turn 740 is positioned at the opening 710. In this configuration, distal sliding of the ablation catheter 724 causes the distal end of the ablation catheter to pass through the opening 710, as shown in FIG. 7f.

Figure 7F:
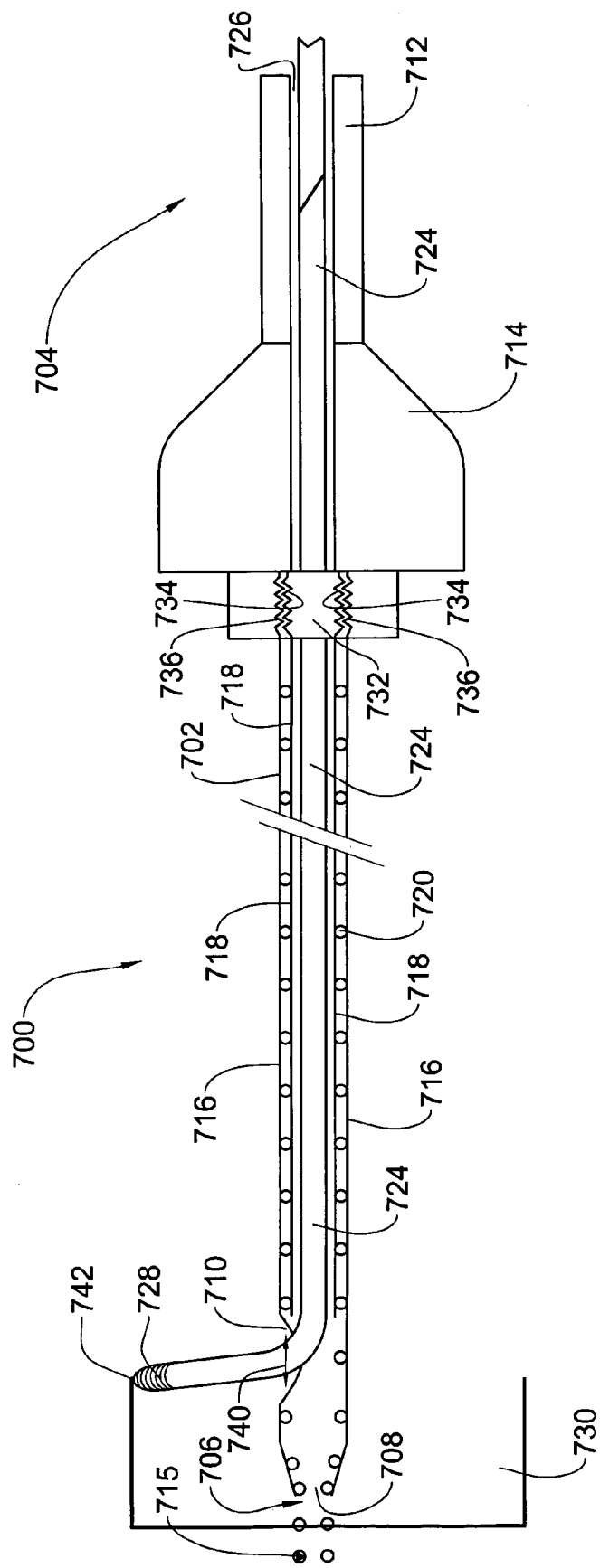

In the configuration of FIG. 7f, the distal end of the ablation catheter 724 extends through the opening 710 and contacts body tissue at a location 742. Ablation energy may then be delivered to the ablation catheter so as to cause ablation of the tissue at the location 742.

The opening 710 occupies an arc in the wall of the inner sleeve 718 that preferably occupies about 180° of the circumference of the shaft 702. In this case, the ablation catheter may be rotated in the inner sleeve about the longitudinal axis of the shaft 702 by grasping the exposed portion of the ablation catheter extending from the handle 712 and rotating the exposed portion of the ablation catheter. In this way, the exposed portion of the ablation catheter extending from the opening 710 will sweep out an arc of up to about 180° as the ablation catheter is rotated in the inner sleeve 718. The direction from which the ablation catheter extends from the opening 710 may thus be selected. Also, the position of the distal end of the ablation catheter in the body cavity 730 may be changed by longitudinal displacement of the shaft 702 of the delivery catheter. Moreover, applying ablation energy to the ablation catheter 724 as the distal end of the ablation catcher is moved in the body cavity 730 allows linear ablation to be carried out on the wall of the body cavity 730.

When tissue ablation has been completed, the ablation catheter 724 is pulled proximally so as to retract the distal end of the ablation catheter 724 in the inner sleeve 718 50 as to regain the configuration shown in FIG. 7e. The distal end of the helical spring is then unscrewed from the tissue 738 by rotating the controller counter clockwise when viewed from the proximal end back to its original position, as determined by the graduations 713 on the controller, so as to bring the delivery catheter back to the configuration shown in FIG. 7d. The delivery catheter 700 is then removed form the body.

Figure 7G:
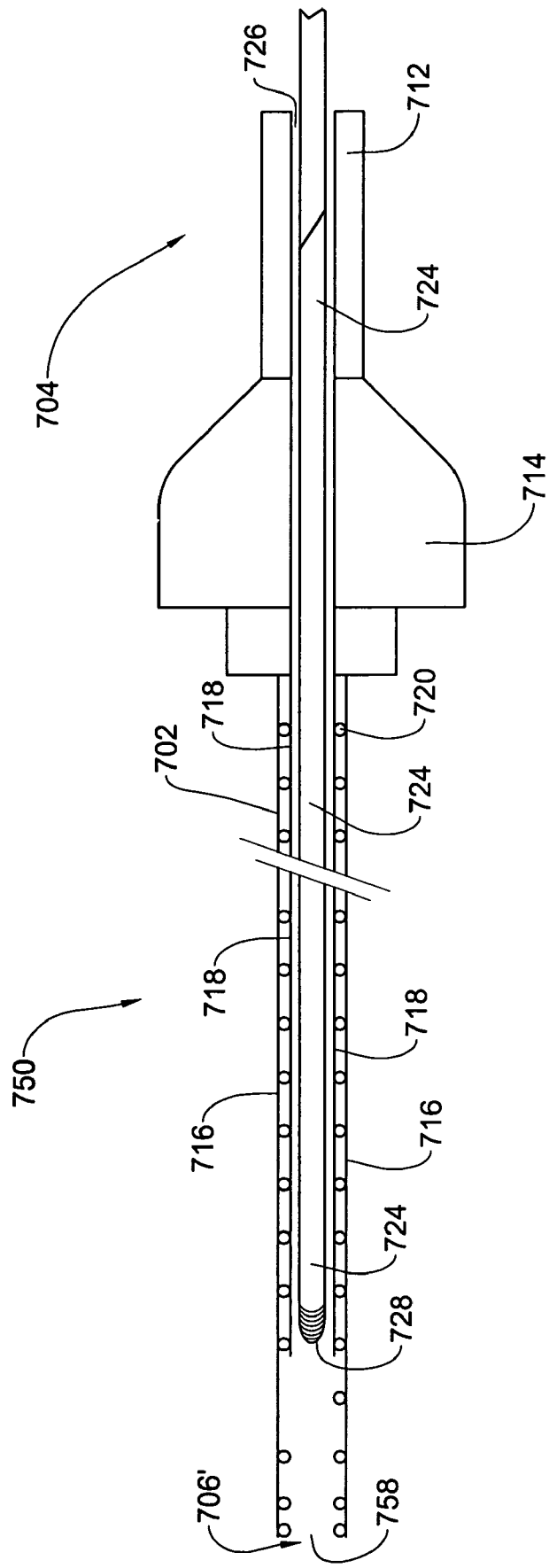

FIG. 7g shows an alternative arrangement 750 of the delivery catheter 700 having a distal end 706'. In the arrangement 750, the distal end 706' is not tapered and there is no side opening 710 as in the arrangement of the distal end 706 shown in FIGS. 7a to 7f.

Figure 7H:
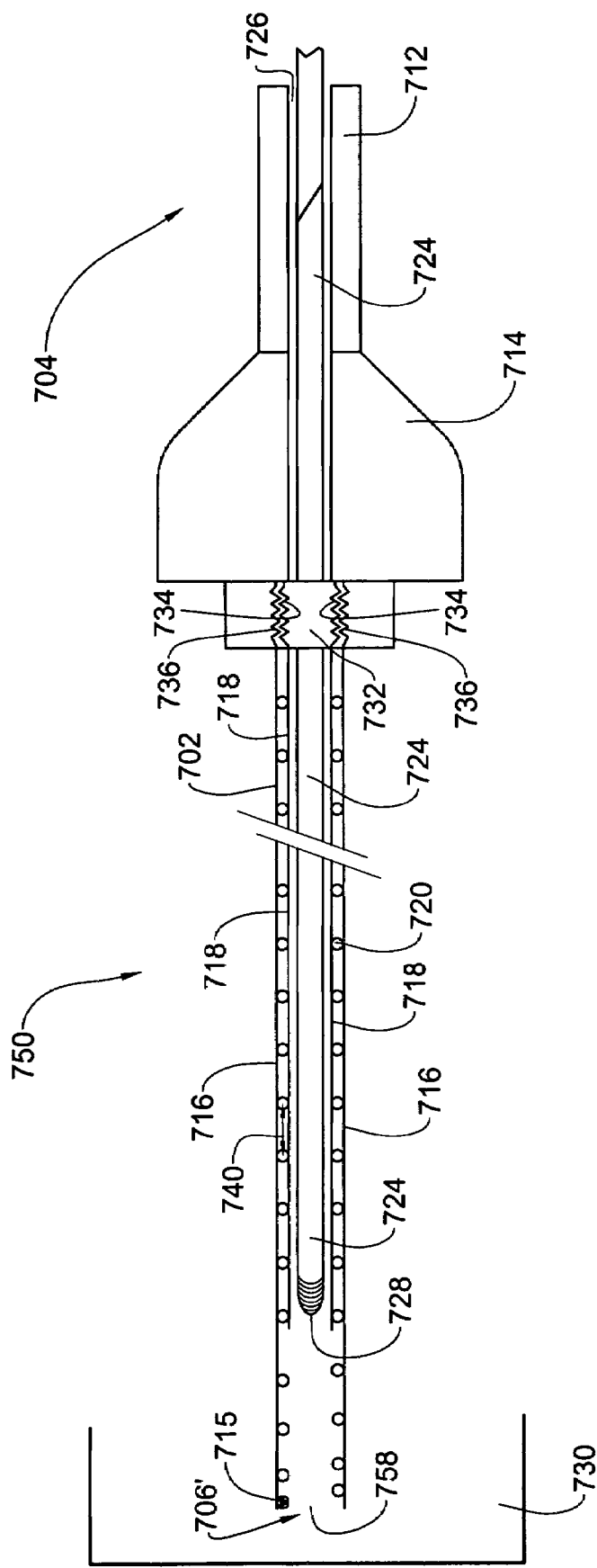
Figure 71:
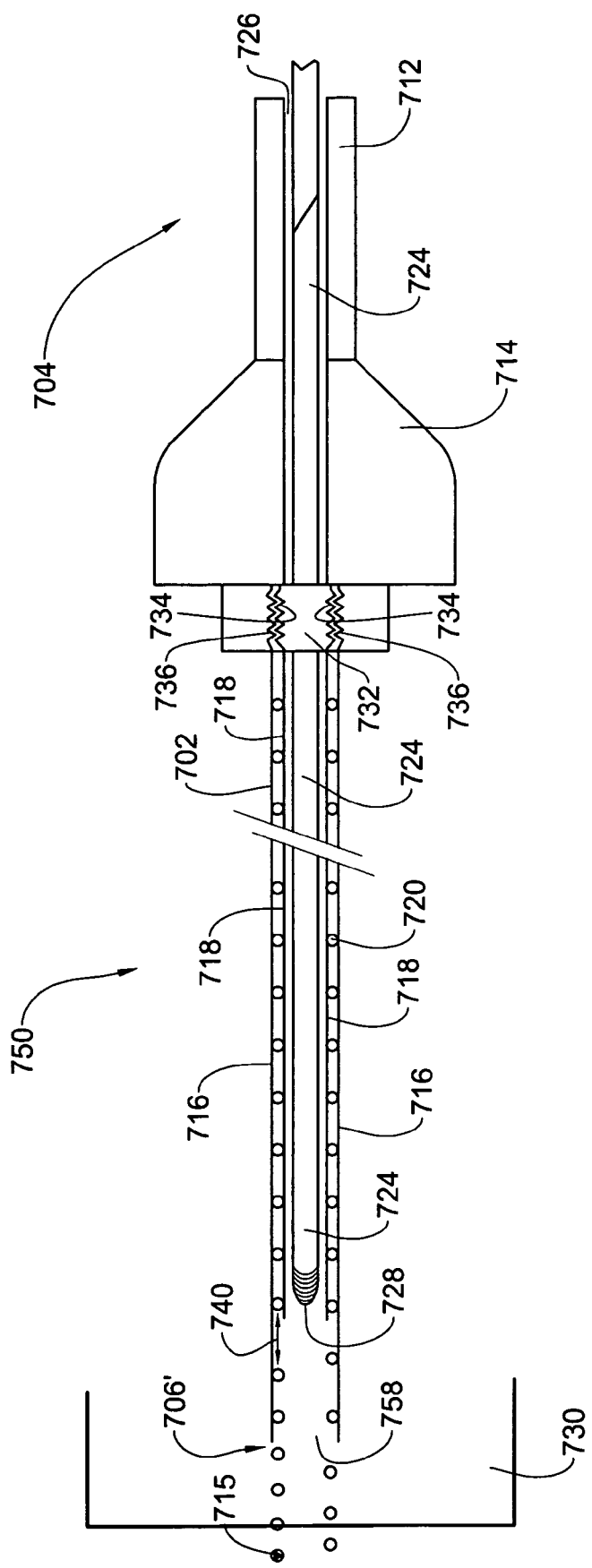
Figure 7J:
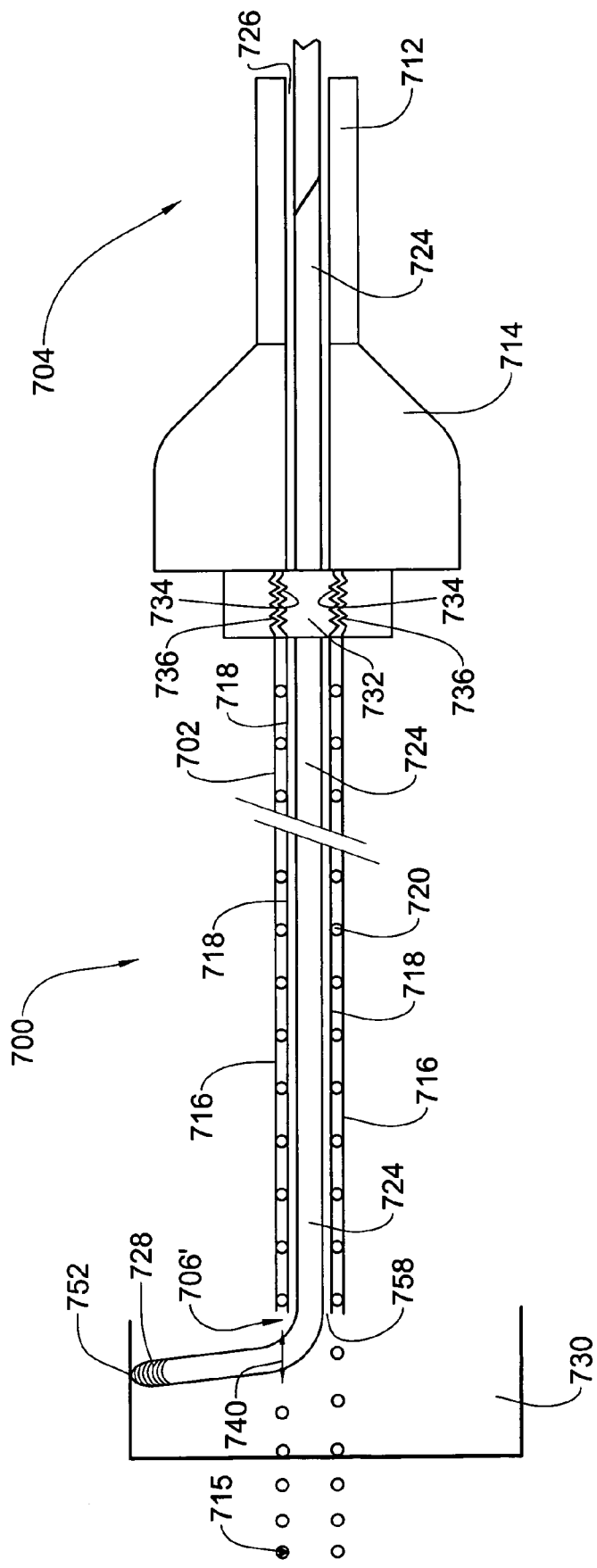

FIG. 7h shows the delivery catheter 750 with the distal end 706' after having been delivered to a body site where ablation is to be carried out. The site may be, for example, a body cavity 730 such as a heart ventricle. With the delivery catheter 750 in the arrangement shown in FIG. 7h, the control 714 is rotated so as to press upon the spring 720 as explained above with reference to FIG. 7a to 7f. Pressing upon the spring 720 in this way causes the spring 720 to rotate inside the shaft 702 and to move distally through the shaft 720, so that the distal end of the spring 720 passes through the distal opening 758 and extends beyond the distal end 706' of the shaft 720. The distal end 706' is maintained a certain distance away from the wall of the cavity 730 as shown in FIG. 7h so as to allow the ablation catheter 724 to exit through the opening 758, as explained below.

Thus, as the spring 720 continues to be rotated, the portion of the spring 720 extending beyond the opening 758 screws into the body tissue 738 in the wall of the cavity 730, with the distal end 706' separated from the wall of the cavity 730, as shown in FIG. 7i.

At this point, the distal end of the ablation catheter 724 is made to pass through the opening 758. This is carried out by grasping the exposed part 725 of the ablation catheter 724 extending from the opening 726 in the handle 712 and sliding the ablation catheter 724 distally. The spacing between adjacent turns of the helical spring 720 is less than the diameter of the ablation catheter, so that the ablation catheter is prevented from passing between adjacent turns of the spring 720. However, one turn of the spring 720, indicated by the arrow 740 in FIGS. 7g and 7h is wider than the other turns of the helical spring 720. The spacing of the turn 740 is greater that the diameter of the ablation catheter 724 and in the configuration of the delivery catheter 700 shown in FIG. 7g, with the helical spring 720 screwed into the tissue 738, the turn 740 is positioned beyond the opening 758 so as to be exposed in the cavity 730. In this configuration, distal sliding of the ablation catheter 724 causes the distal end of the ablation catheter to pass through the opening 758 and between the turn 740, as shown in FIG. 7i.

In the configuration of FIG. 7i, the distal end of the ablation catheter 724 extends through the opening 758 and contacts body tissue at a location 752. Ablation energy may then be delivered to the ablation probe so as to cause ablation of the tissue at the location 742.

The ablation catheter may be rotated in the inner sleeve about the longitudinal axis of the shaft 702 by grasping the exposed portion of the ablation catheter extending from the handle 712 and rotating the exposed portion of the ablation catheter. In this way, the exposed portion of the ablation catheter extending from the opening 710 will sweep out an arc of up to almost 360. as the ablation catheter is rotated in the inner sleeve 718. The direction from which the ablation probe extends from the opening 758 may thus be selected. Also, the position of the distal end of the ablation catheter in the body cavity 730 may be changed by longitudinal displacement of the shaft 702 of the delivery catheter. Moreover, applying ablation energy to the ablation catheter 714 as the distal end of the ablation catheter is moved in the body cavity 730 allows linear ablation to be carried out on the wall of the body cavity 730.

Figure 8C:
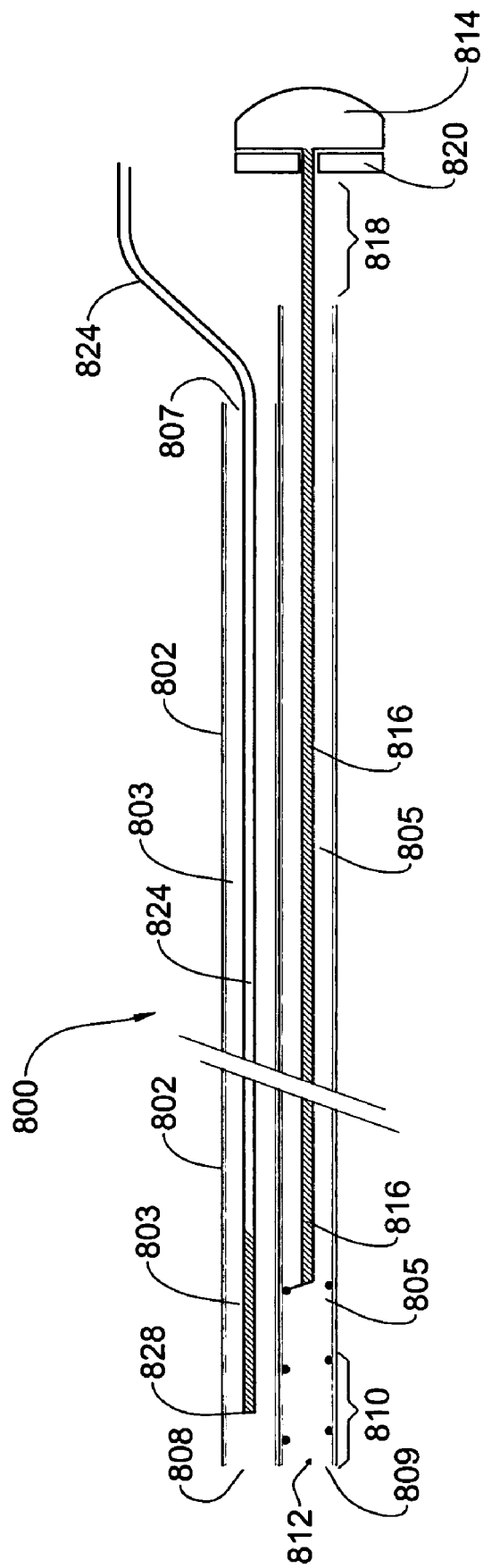
FIG. 8 shows a delivery catheter for an ablation device in accordance with another embodiment of the invention.

Referring now to FIG. 8, FIGS. 8a to 8f shows a delivery catheter 800 for delivering a tissue ablation probe to a body site, in accordance with another embodiment of the invention. As seen in FIG. 8a, the delivery catheter 800 has a flexible shaft 802 having a proximal end 804 and a distal end 806. The shaft 802 contains two lumens 803 and 805. The lumen 803 has an opening 807 at its proximal end, and an opening 808 at its distal end. The lumen 803 is configured to receive an ablation catheter, as explained below. The lumen 805 has an opening 809 at its distal end and an opening 815 at its proximal end. The lumen 805 contains an attaching member that is retracted into the lumen 805 during delivery of the distal end 806 of the catheter 800 to a body site, and is then made to extend through the opening 809 to attach to a tissue surface, as explained below. Movement of the attaching member in the lumen 805 is controlled by a controller 814 located at the proximal end 804 of the lumen 805, as explained below.

FIG. 8b shows the delivery catheter 800 in longitudinal section. The attaching mechanism includes a helical element 810 that terminates in a sharp point 812. The helical element 810 is attached to the controller 814 by a flexible rod 816 that extends along the length of the lumen 805 from the helical element 810 to the controller 814. Rotation of the controller 814 relative to a fixed ring 820 drives rotation of the rod 816 which in turn drives rotation of the helical element 810. Longitudinal movement of the controller 814 drives longitudinal movement of the rod 816 which in turn drives longitudinal movement of the helical element 810. Thus, longitudinal movement of the controller 814 from its position shown in FIG. 8b in which a gap 818 between the controller 814 and the distal end of the lumen 805 towards the distal end 806 of the lumen 805 causes the helical member 810 to move through the opening 809 so as to extend beyond the distal end of the lumen 809, as shown below.

The lumen 808 is configured to receive in its lumen the shaft of an ablation catheter. FIG. 8c shows the delivery catheter 800 after an ablation catheter 824 has been inserted into the lumen 808. The ablation catheter is inserted through the opening 807 at the distal end of the lumen 808 and is slid through the lumen 808 until the distal end of the ablation catheter 824 is located at the distal end of the lumen 808. The ablation catheter 824 may be any type of ablation catheter known in the art and may use any type of ablative energy, such as radio frequency (RF) energy or cryo energy. The ablation catheter is connected at a proximal end (not shown) to a source of ablative energy (also not shown). The distal end of the ablative catheter includes a probe 828 for delivering ablative energy to a body tissue, as explained below.

With the delivery catheter 800 and the ablative catheter 824 in the configuration shown in FIG. 8c, the distal end 806 of the delivery catheter is inserted into the body and delivered to a body site where ablation of tissue is to be carried out. For example, a guide wire (not shown) may be inserted into the body through an incision in the skin and then delivered via the vasculature to a body site such as a heart, where ablation is to be carried out. The delivery catheter 800 may then be mounted on the guide wire and the distal end 806 delivered to the site where the ablation is to be carried out on the guide wire. Alternatively, the distal end 806 of the delivery catheter 800 may be delivered to an epicardial site in a surgical procedure.

Figure 8D:
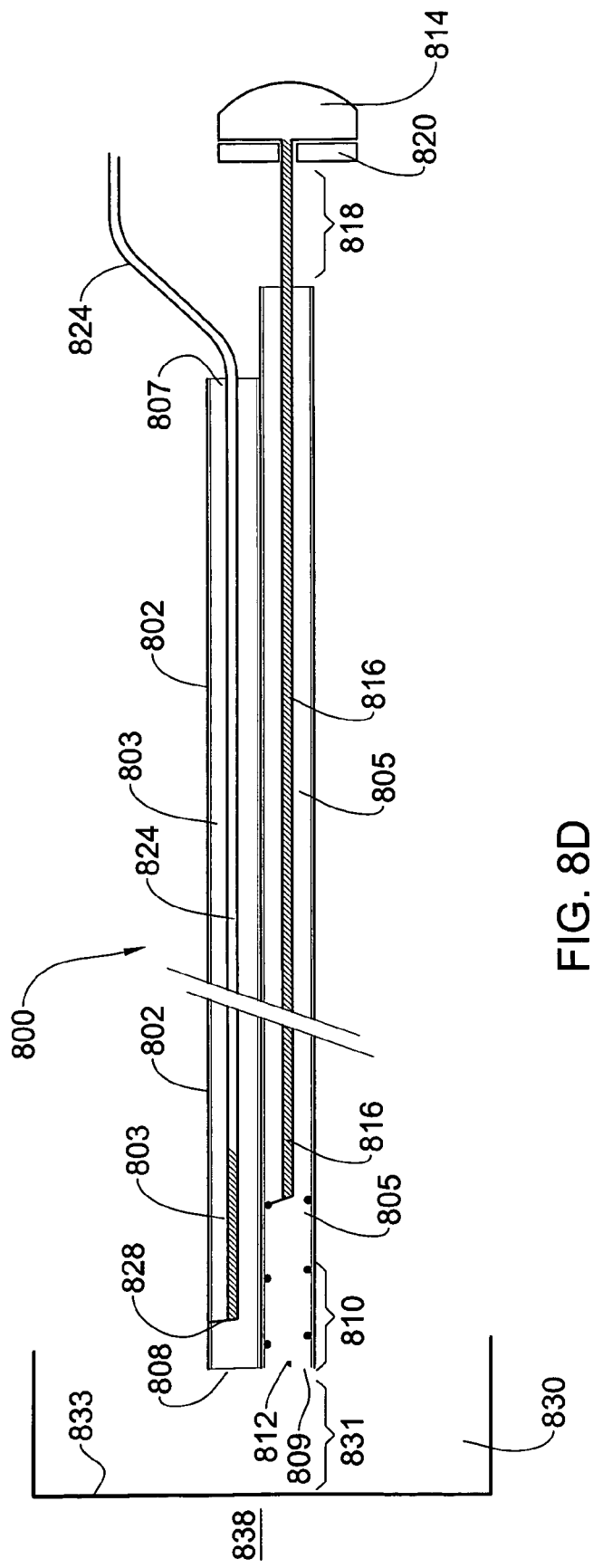
Figure 8E:
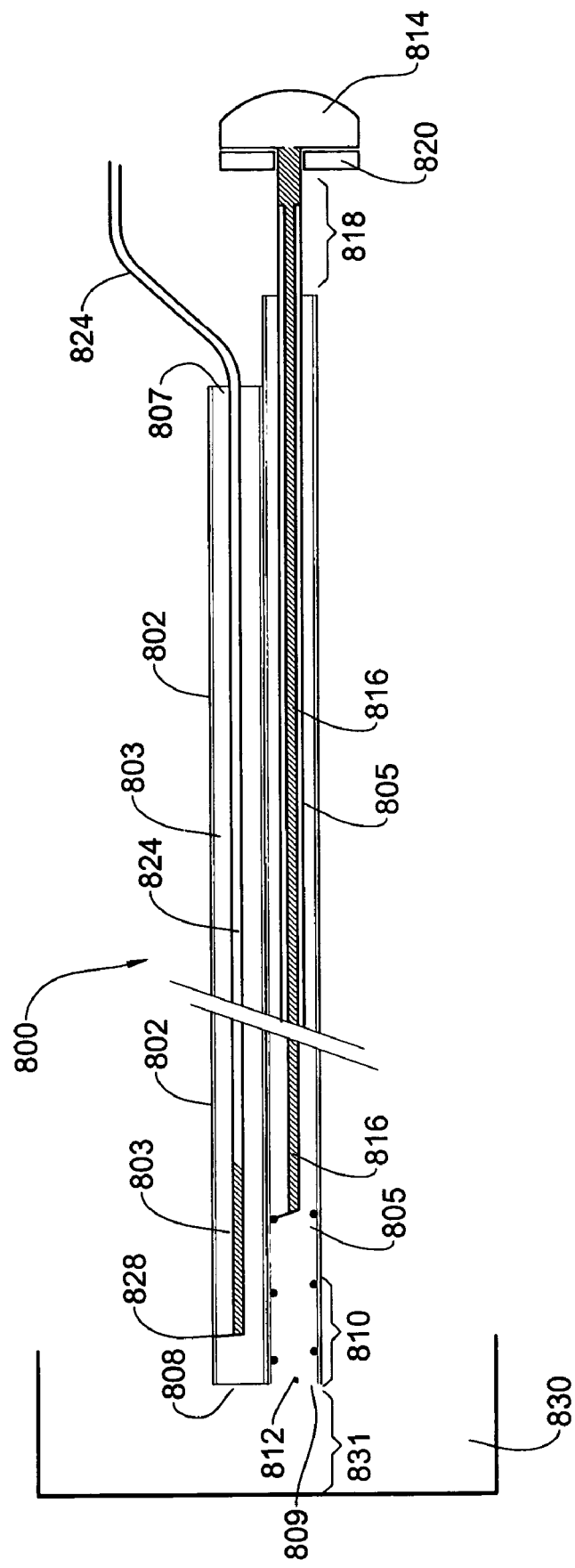

FIG. 8d shows the delivery catheter 800 after having been delivered to a body site where ablation is to be carried out. The site may be, for example, a body cavity 830 such as a heart ventricle. With the delivery catheter 800 in the arrangement shown in FIG. 8d, with a gap 831 between the distal end 806 and the tissue surface 833, the control 814 is moved longitudinally towards the distal end 806, 50 as to cause the helical member 810 to pass through the opening 809 and to extend beyond the distal end of the lumen 805, as shown in FIG. 8e.

Figure 8F:
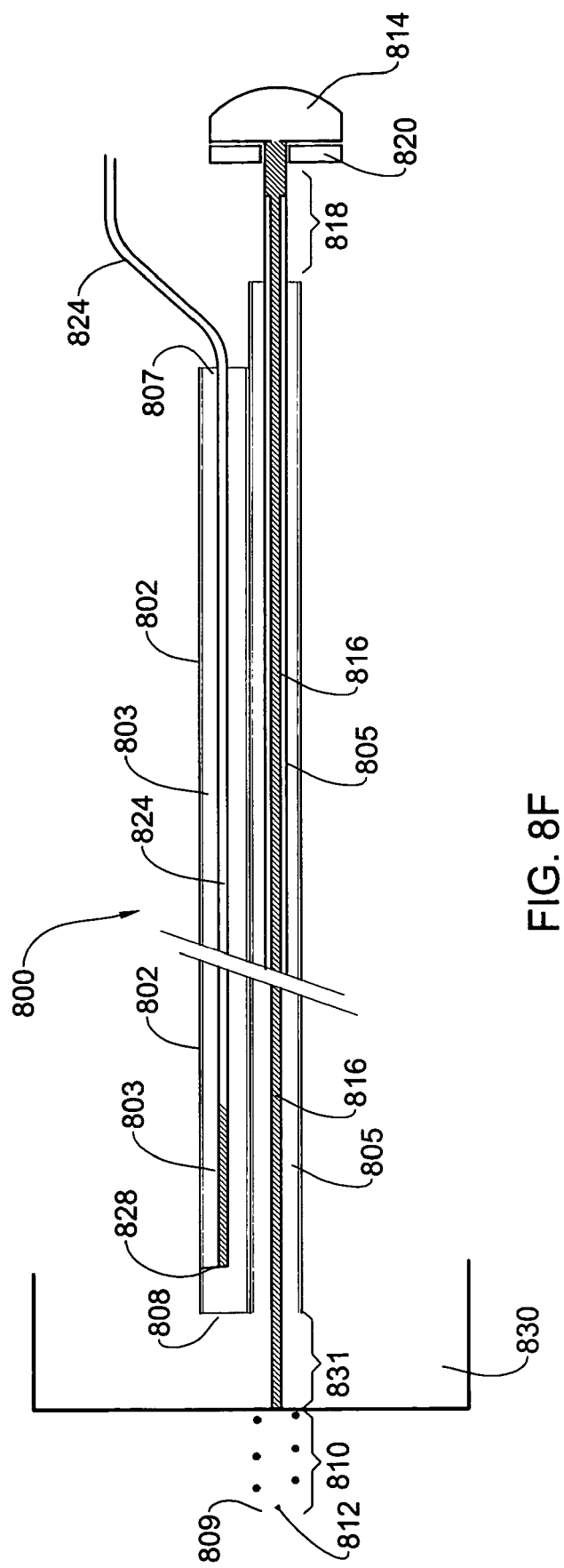

At this point, controller 814 is rotated in a clockwise direction when viewed from the proximal end 804. As explained above, rotation of the controller 814 drives rotation of the helical element 810. The helical element 810 terminates at its distal end in a sharp point 812. Thus, as the controller 814 continues to be rotated, the helical element 810 screws into the body tissue 838 in the wall of the cavity 830, as shown in FIG. 8f so as to attach the distal end 806 of the delivery catheter 800 to the wall of the cavity 830. As the helical member 810 screws into the wall of the cavity 830, the controller 814 is drawn further towards the proximal end of the lumen 805. Graduation marks 813 on the controller 814 (see FIG. 8a) indicate the amount the controller 814 has been rotated from its original position. The controller 814 is provided with a locking mechanism (not shown) that prevents unwanted rotation of the controller.

Now the distal end of the ablation catheter 824 is made to pass through the opening 808 at the distal end of the lumen 803. This is carried out by grasping the exposed part 825 of the ablation catheter 824 extending from opening 807 at the proximal end of the lumen 803 sliding the ablation catheter 824 distally as shown in FIG. 8g.

Figure 8G:
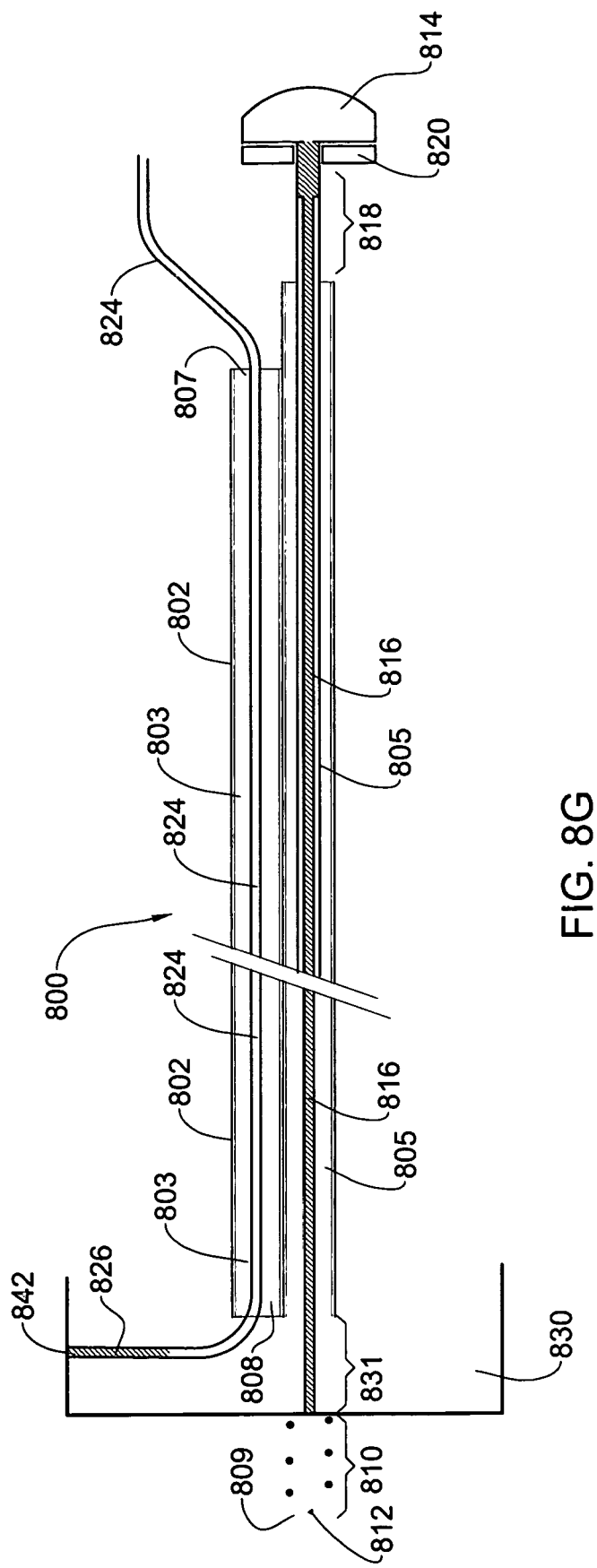

In the configuration of FIG. 8g, the distal end of the ablation catheter 824 extends through the opening 808 and contacts body tissue at a location 842. Ablation energy may then be delivered to the ablation catheter so as to cause ablation of the tissue at the location 842.

The ablation catheter 824 may be rotated in the lumen 803 about the longitudinal axis of the lumen 803 by grasping the exposed portion 825 of the ablation catheter extending from the lumen 803 and rotating the exposed portion 825 of the ablation catheter. In this way, the exposed portion of the ablation catheter extending from the opening 808 can be made to sweep out an arc of up to 360° as the ablation catheter is rotated in the lumen 803. The direction from which the ablation probe extends from the opening 808 may thus be selected. Applying ablation energy to the ablation probe 828 as the distal end of the ablation catcher is moved in the body cavity 830 allows linear ablation to be carried out on the wall of the body cavity 830.

When tissue ablation has been completed, the ablation catheter 824 is pulled proximally so as to retract the distal end of the ablation catheter 824 into the lumen 803 so as to regain the configuration shown in FIG. 8f. The helical element 810 is then unscrewed from the tissue 838 by rotating the controller counter clockwise when viewed from the proximal end back to its original position, as determined by the graduations 813 on the, so as to bring he deliver catheter back to the configuration shown in FIG. 8d. The delivery catheter 800 is then removed form the body.

Figure 2:
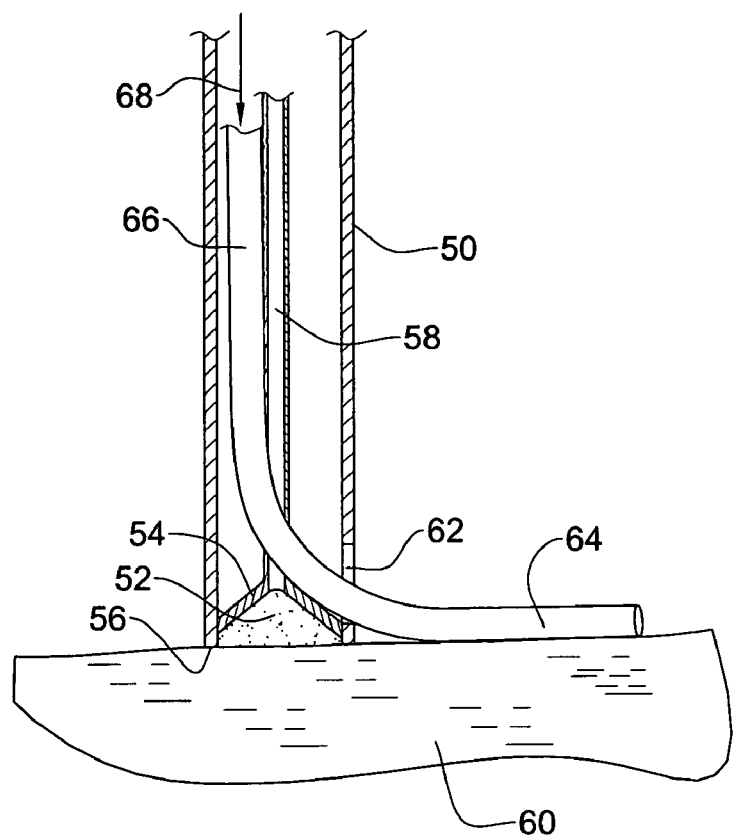
FIG. 2 shows a delivery catheter in accordance with another embodiment of the invention having a vacuum attachment mechanism, illustrated in a state in which it is attached to a tissue surface with the ablation probe in contact with tissue.

Reference is now being made to FIG. 2 which is a longitudinal section through an end portion of a catheter 50. Formed at the end of the catheter 50 is a space 52 defined between septum 54 and rim 56. Space 52 opens to vacuum duct 58 that leads to a vacuum source (not shown). The formation of the vacuum within space 52 allows for the firm attachment of catheter 50 to a tissue portion 60, such as a heart muscle tissue. The side wall of catheter 50 has an opening 62 permitting extraction of the probe 64 of catheter 66 (through pushing the catheter longitudinally in the direction of arrow 68 so as to bring it into contact with the tissue portion 60.

Figure 1A:
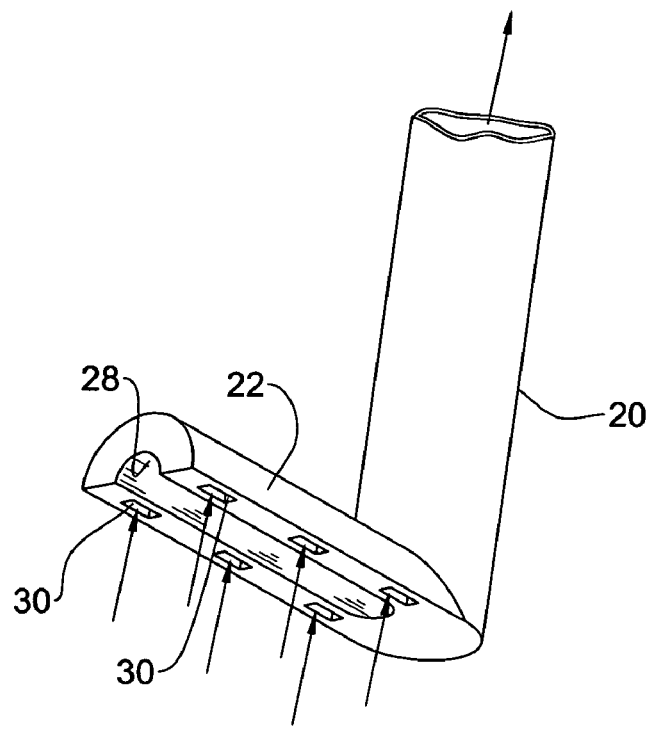
FIG. 1A shows a bottom perspective view of the distal end of a delivery catheter in accordance with an embodiment of the invention having a vacuum attachment to a tissue surface.
Figure 1B:
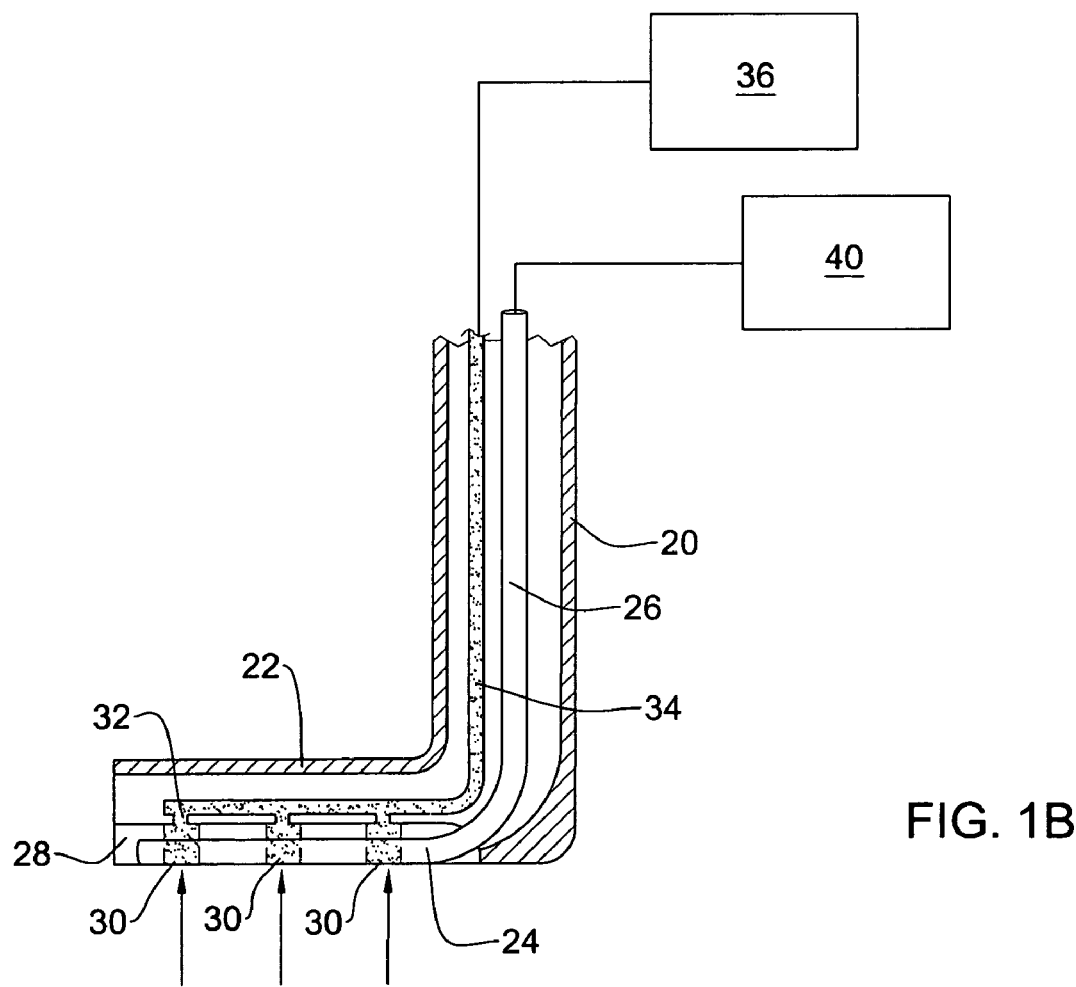
FIG. 1B is a longitudinal cross-section through the delivery catheter of FIG. 1A, accommodating an ablation probe.

Reference is now being made to FIGS. 1A and 1B showing the end portion of a guiding catheter 20 having an attachment body 22 for attachment of an ablation probe 24 of an ablation catheter 26 to tissue. The attachment body 22 is oriented essentially in a right angle to the longitudinal axis of catheter 20 (as will be appreciated this right angle orientation is but an example and the angle may also be other than right angle) and has a trough-like recess 28 that accommodates the ablation probe 24. Formed in its bottom face are a plurality of openings 30 that are linked through an internal cavity 32 to a vacuum duct 34 that leads to a vacuum source 36. It is through this vacuum arrangement that the attachment body can firmly attach to a tissue whereby the ablation probe 24 of the ablation catheter 26 rests against a tissue portion to be ablated. The ablation catheter is linked to a unit 40 for delivering of the ablation energy to the ablation probe. The ablation energy may be, for example, a cold fluid for cryo type ablation, etc.

Figure 3A:
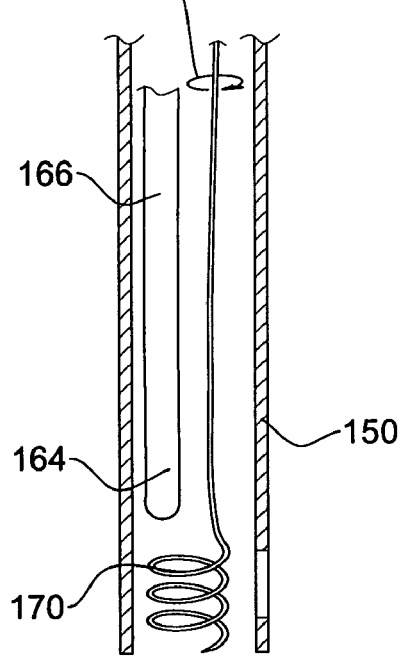
FIG. 3A shows a delivery catheter accommodating an ablation probe with a helical attachment member for a screw-type engagement to tissue.
Figure 3B:
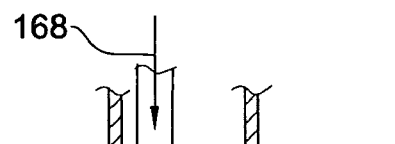
FIG. 3B shows the delivery catheter of FIG. 3A with the helical attachment member engaged into the tissue and with an ablation probe in contact with tissue.
Figure 4A:
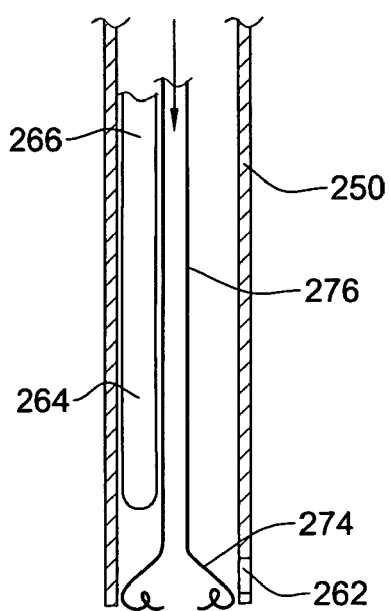
FIG. 4A shows a delivery catheter with an attachment mechanism in accordance with another embodiment of the invention that comprises hooks that are strained within the catheter that once released can be inserted into a tissue for attachment of the distal end of the catheter to the tissue.
Figure 4B:
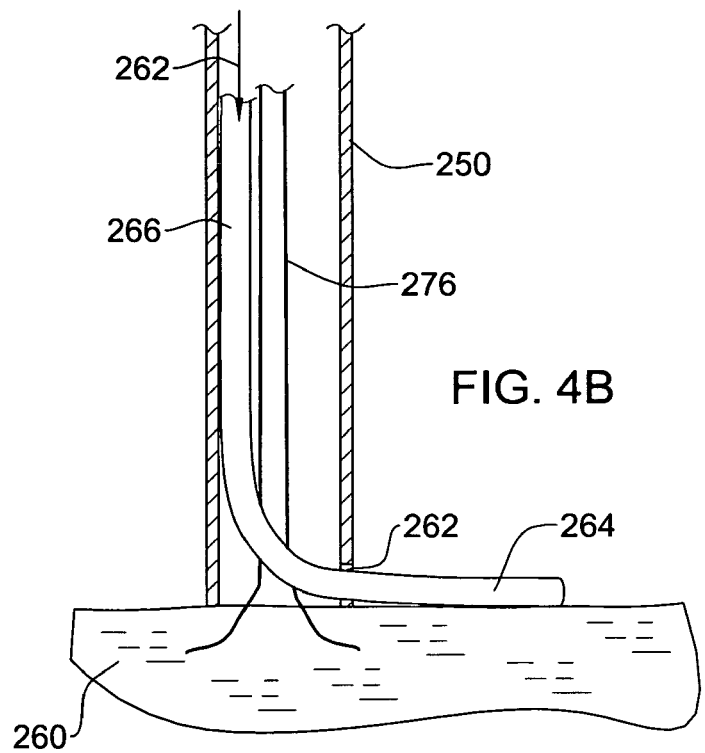
FIG. 4B shows the hooks after being released and inserted into a tissue with the probe resting against the tissue.
Figure 5A:
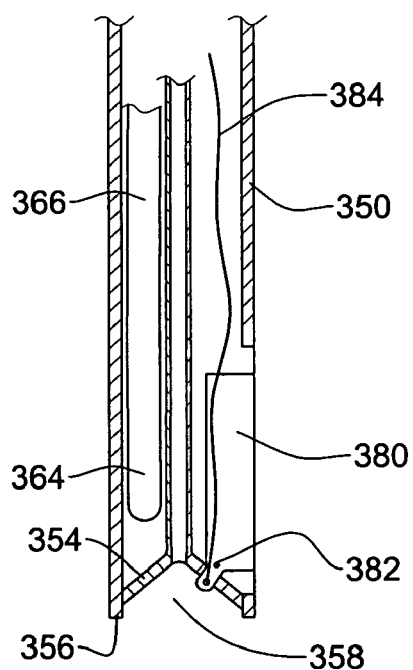
FIG. 5A shows a delivery catheter in accordance with the invention with an attachment mechanism that includes a vacuum attachment arrangement combined with deployable trough-like member that can accommodate and firmly hold an ablation probe to a tissue.
Figure 5B:
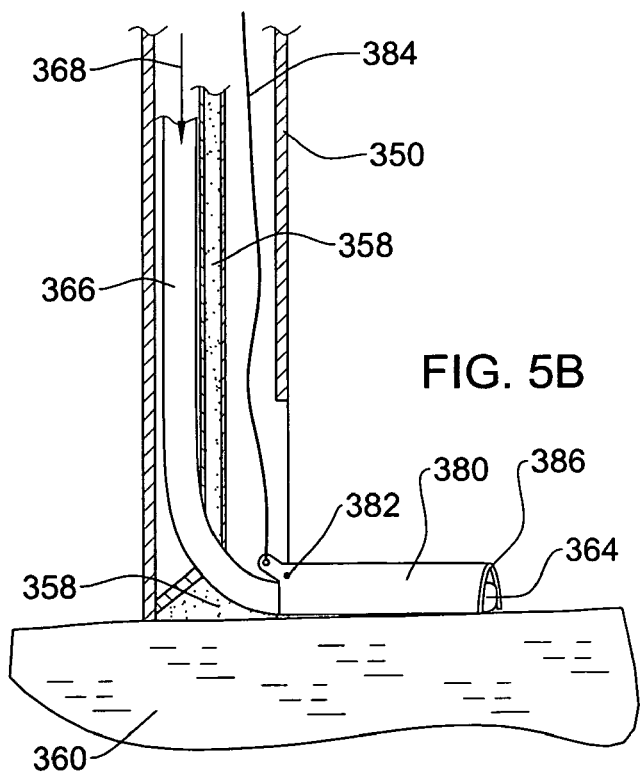
FIG. 5B shows the delivery catheter of FIG. 5A attached to a tissue with the trough-like member deployed and firmly holding an ablation catheter to a tissue.

In the description of other embodiments, like elements to those in the embodiment of FIG. 2 will be given like reference numerals shifted by 100 for FIGS. 3A and 3B, 200 for FIGS. 4A and 4B, 300 for FIGS. 5A and 5B and 400 for FIGS. 6A and 6B (for example elements 150 and 164 in FIGS. 3A and 3B and elements 250 and 264 in FIGS. 4A and 4B are functionally the same as elements 50 and 64 in FIG. 2, respectively; etc.). The reader is referred to the description of FIG. 2 for explanation of their function.

FIG. 3 shows another embodiment of the distal end of a delivery catheter of the invention of the distal end of a delivery catheter of the invention. The attachment mechanism in the embodiment of the distal end of a delivery catheter of FIG. 3 comprises a helical attachment member 170 that screws into a tissue when rotated as indicated by arrow 172 thereby attaching the catheter 150 to tissue 160 as shown in FIG. 3B. Ablation probe 164 then attaches to tissue 160 in a manner similar to that of FIG. 2.

FIG. 4 shows another embodiment of the distal end of a delivery catheter of the invention. The delivery catheter of the embodiment of FIG. 4 includes an attachment mechanism comprising hooks 274 that are held in a strained state within the distal end and once released, by pushing distally on members 276 can become inserted into a tissue, to hold the catheter firmly against the tissue 260 as seen in FIG. 4B.

FIG. 5 shows another embodiment of the distal end of a delivery catheter of the invention. The delivery catheter of the embodiment of FIG. 5 includes an attachment mechanism comprising, in addition to a vacuum type attachment similar to that of the embodiment of FIG. 2, a releasable sleeve member 380 that can rotate about a pivot 382 by pulling on wire 384. Once the wire 384 is pulled, member 380 rotates and can accommodate probe 364 of ablation catheter 366 within its trough-like recess 386 to hold probe 364 firmly against tissue 360.

Figure 6A:
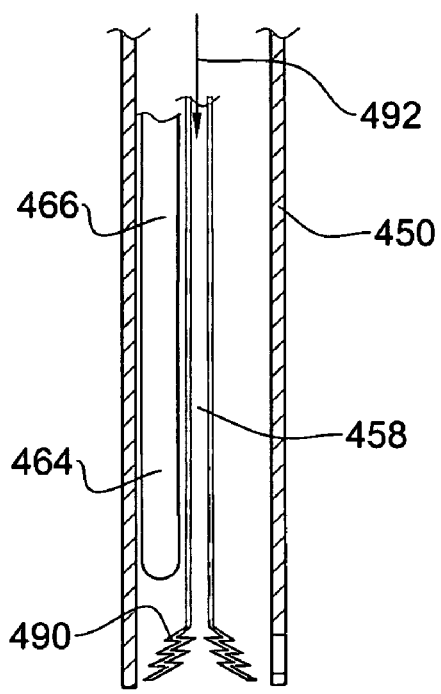
FIG. 6A shows a delivery catheter in accordance with another embodiment of the invention with an attachment mechanism that includes a vacuum-type attachment arrangement involving a vacuum cup held in a folded and strained state in the distal end of the catheter that can be released from the distal end.
Figure 6B:
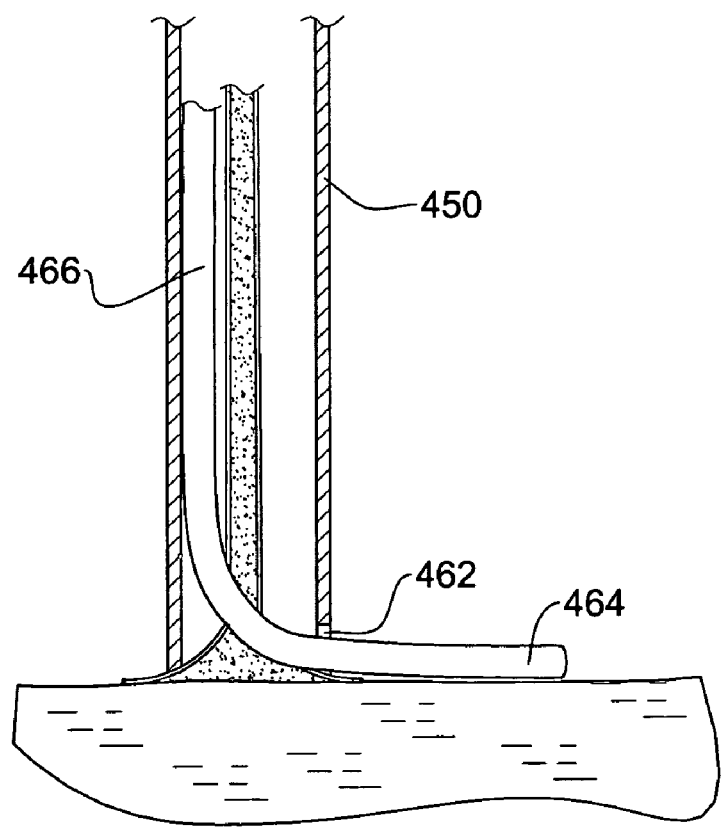
FIG. 6B shows the catheter of FIG. 5A attached to a tissue with the vacuum cup fully opened firmly attached to a tissue.

FIG. 6 shows another embodiment of the distal end of a delivery catheter of the invention. The distal end of the delivery catheter comprises an attachment mechanism including a vacuum cup 490 that is made of a flexible material such as silicone rubber and that in a configuration seen in FIG. 6A for delivery of the distal end to a body site where tissue ablation is to be carried out, maintained in a strained state with the end of the catheter. After delivery of the distal end to the body site, the vacuum cup is pushed distally and thus opens to a deployed position seen in FIG. 6B to yield a fully operational vacuum cup. The vacuum cup is linked to a vacuum duct 458 linked to a vacuum source (not shown).

The invention claimed is:

1. A delivery catheter having a shaft with a distal end and a proximal end for delivering an ablation probe to a body site, comprising: (a) a mounting member located at the distal end configured to receive an ablation probe; and (b) at least one attachment member configured to attach the distal end to a tissue surface, wherein the at least one attachment member includes a helical wire configured to be rotated so as to screw into a body tissue, and further comprising a controller located at the proximal end of the shaft, rotation of the controller being coupled to rotation of the helical wire; and wherein the delivery catheter is configured to allow an ablation probe when mounted on the distal end to be manipulated through adjacent turns of the helical wire so as to extend from the distal end in a direction selected from a range of directions.

2. The delivery catheter according to claim 1 further configured to allow an ablation probe when mounted on the distal end to be manipulated so as to move along a tissue surface and perform linear ablation.

3. The delivery catheter according to claim 1 wherein the range of directions is determined by a hole in the shaft.

4. The delivery catheter according to claim 3 wherein the shaft has a circumference and the hole occupies an arc of the circumference.

5. The delivery catheter according to claim 4 wherein the arc extends for about 180° of the circumference.

6. The delivery catheter according to claim 1 wherein the controller is provided with graduations so as to provide an indication of the extent to which the helical wire has been rotated.

7. The delivery catheter according to claim 1 wherein rotation of the controller is coupled to rotation of the helical wire by a helical spring extending in the shaft from the controller to the helical wire.

8. The delivery catheter according to claim 7 configured to allow a portion of the helical spring to extend through the distal end of the delivery catheter and to allow an ablation catheter to pass through adjacent turns of the helical spring in the extended portion and to be rotated through an angle of 360° after passing between the turns of the helical spring.

9. The delivery catheter according to claim 1 configured to be mounted on a guide wire.

10. A medical system comprising: a delivery catheter according to claim 1; and a tissue ablation device having an ablation probe; wherein the delivery catheter and the ablation probe are configured to allow the ablation probe to be mounted at the distal end of the delivery catheter.

11. The medical system according to claim 10 further comprising a utility for delivering an ablative energy to the ablation probe.

12. The medical system according to claim 10 wherein the delivery catheter is configured to be mounted on a guide wire and the system further comprises a guide wire.

13. A medical system according to claim 10 wherein the ablation probe is straight.

14. A medical system according to claim 10, for use in ablation of heart tissue.

15. A medical system according to claim 10 wherein the ablating energy is selected from Radio-Frequency (RF), microwave, laser, ultrasound and cryo.

16. A medical system according claim 14, wherein said ablation probe is configured for intra-heart catheterization in which the ablation probe ablates the heart tissue from within the heart.

17. A method for ablating a body tissue, comprising: (a) mounting an ablation probe onto the distal end of a delivery catheter according to claim 1; (b) delivering the distal end of the delivery catheter to a body site where tissue ablation is to be performed; (c) attaching the distal end of the delivery catheter to a tissue surface; (d) extending the ablation probe from the distal end of the delivery catheter and manipulating the ablation probe so as to contact one or more desired locations on a tissue surface at the site where ablation is to be performed; and (e) applying ablative energy to the tissue at each of the one or more desired locations at an intensity and for time to yield effective tissue ablation.

18. The method according to claim 17 wherein the ablation probe is moved over the tissue surface as ablative energy is applied to the tissue surface so as to perform linear ablation.

19. The method according to claim 17, wherein said probe is any one selected from Radio-Frequency (RF) probe, microwave probe, laser probe and ultrasound probe.

\* \* \* \* \*